(12) United States Patent
Ou-Yang et al.

(10) Patent No.: US 8,512,294 B2
(45) Date of Patent: Aug. 20, 2013

(54) VASCULAR ACCESS DEVICE ANTIMICROBIAL MATERIALS AND SOLUTIONS

(75) Inventors: David Ou-Yang, Woodbury, MN (US); Wayne K. Rasmussen, Riverdale, UT (US); Glade H. Howell, Sandy, UT (US); Lantao Guo, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 947 days.

(21) Appl. No.: 11/829,010

(22) Filed: Jul. 26, 2007

(65) Prior Publication Data

US 2008/0161763 A1 Jul. 3, 2008

Related U.S. Application Data

(60) Provisional application No. 60/820,706, filed on Jul. 28, 2006.

(51) Int. Cl.
*A61M 5/178* (2006.01)

(52) U.S. Cl.
USPC ............. 604/167.04; 604/167.03; 604/256; 604/265

(58) Field of Classification Search
USPC ............. 604/167.01–167.04, 167.06, 246, 604/249, 256, 265, 513
See application file for complete search history.

(56) References Cited

U.S. PATENT DOCUMENTS

| | | | |
|---|---|---|---|
| 4,765,588 A | 8/1988 | Atkinson | |
| 4,895,566 A | 1/1990 | Lee | |
| 4,925,668 A * | 5/1990 | Khan et al. | 424/422 |
| 4,985,399 A * | 1/1991 | Matsuda et al. | 503/227 |
| 5,217,493 A | 6/1993 | Raad et al. | |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,366,505 A | 11/1994 | Farber | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,540,661 A * | 7/1996 | Tomisaka et al. | 604/265 |
| 5,549,651 A | 8/1996 | Lynn | |
| 5,638,812 A | 6/1997 | Turner | |
| 5,716,406 A | 2/1998 | Farber | |
| 5,957,898 A | 9/1999 | Jepson et al. | |
| 6,171,287 B1 | 1/2001 | Lynn et al. | |
| 6,261,282 B1 | 7/2001 | Jepson et al. | |
| 6,344,033 B1 | 2/2002 | Jepson et al. | |
| 6,475,434 B1 | 11/2002 | Darouiche | |
| 6,579,539 B2 | 6/2003 | Lawson et al. | |
| 6,595,964 B2 | 7/2003 | Finley et al. | |
| 6,651,956 B2 | 11/2003 | Miller | |
| 6,669,681 B2 | 12/2003 | Dudar et al. | |
| 6,719,991 B2 | 4/2004 | Darouiche et al. | |
| 6,723,350 B2 | 4/2004 | Burrell et al. | |

(Continued)

*Primary Examiner* — Emily Schmidt (74) *Attorney, Agent, or Firm* — Jeanne Lukasavage; Craig Metcalf; Kirton McConkie (57) ABSTRACT

A medical device includes an antimicrobial layer. A method of depositing an antimicrobial agent on or in the body of a medical device includes inserting a high temperature resistant tube having multiple holes through its surface into a vascular access device and coating, or delivering an antimicrobial agent to, and interior surface of the device.

14 Claims, 7 Drawing Sheets

(56) References Cited

U.S. PATENT DOCUMENTS

| | | |
|---|---|---|
| 6,843,784 B2 | 1/2005 | Modak et al. |
| 6,866,656 B2 | 3/2005 | Tingey et al. |
| 6,887,270 B2 | 5/2005 | Miller et al. |
| 6,908,459 B2 | 6/2005 | Harding et al. |
| 2001/0010016 A1 | 7/2001 | Modak et al. |
| 2002/0009436 A1 | 1/2002 | Doyle et al. |
| 2002/0037260 A1 | 3/2002 | Budny et al. |
| 2002/0064858 A1 | 5/2002 | Yacoby-Zeevi |
| 2002/0091424 A1 | 7/2002 | Biel |
| 2002/0133124 A1* | 9/2002 | Leinsing et al. ............ 604/256 |
| 2002/0193752 A1 | 12/2002 | Lynn |
| 2003/0105143 A1 | 6/2003 | Ammendola et al. |
| 2003/0134783 A1 | 7/2003 | Harshey et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0109852 A1 | 6/2004 | Xu |
| 2004/0132164 A1 | 7/2004 | Doyle et al. |
| 2004/0180829 A1 | 9/2004 | Bassler et al. |
| 2004/0230162 A1 | 11/2004 | Tan |
| 2005/0008671 A1 | 1/2005 | Van Antwerp |
| 2005/0048124 A1 | 3/2005 | Sarangapani |
| 2005/0059731 A1 | 3/2005 | Albrecht et al. |
| 2005/0118239 A1 | 6/2005 | Sabesan |
| 2005/0131356 A1 | 6/2005 | Ash et al. |
| 2005/0143286 A1 | 6/2005 | Singh et al. |
| 2005/0158253 A1 | 7/2005 | Budny et al. |
| 2005/0233950 A1 | 10/2005 | Madhyastha |
| 2005/0256500 A1 | 11/2005 | Fujii |

\* cited by examiner

VASCULAR ACCESS DEVICE ANTIMICROBIAL MATERIALS AND SOLUTIONS

RELATED APPLICATIONS

This application claims the benefit of U.S. Provisional Application No. 60/820,706, filed Jul. 28, 2006, entitled VASCULAR ACCESS DEVICE ANTIMICROBIAL MATERIALS AND SOLUTIONS, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The proximal end of the vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes or seals the vascular access device, and allows for intermittent infusion or injection of fluids and pharmaceuticals. An IV access device may include a housing and a septum for closing the system. The septum may be opened with a blunt cannula or a male Luer of a medical device.

Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Vascular access device infection resulting in CRBSIs may be caused by failure to regularly clean the device, a non-sterile insertion technique, or by pathogens entering the fluid flow path through either end of the path subsequent to catheter insertion. Studies have shown the risk of CRBSI increases with catheter indwelling periods. When a vascular access device is contaminated, pathogens adhere to the vascular access device, colonize, and form a biofilm. The biofilm is resistant to most biocidal agents and provides a replenishing source for pathogens to enter a patient's bloodstream and cause a BSI. Thus, what are needed are systems, devices, and methods to reduce the risk and occurrence of CRBSIs.

BRIEF SUMMARY OF THE INVENTION

The present invention has been developed in response to problems and needs in the art that have not yet been fully resolved by currently available vascular access systems, devices, and methods. Thus, these systems, devices, and methods are developed to reduce the risk and occurrence of CRBSIS.

A medical device may be a vascular access device including a surface and a layer of the device that may include an antimicrobial agent. The layer of the device may be compounded with or integrated into the material of the body of the vascular access device. The body of the vascular access device may include a septum housed within the body. The septum may include a slit with a surface.

The layer may include a solution containing a mixture of the antimicrobial agent and a lube oil that coats the surface of the slit. A second layer in contact with the layer of the device may include a lube oil with a low coefficient of friction. The layer may include a polymeric coating with a low coefficient of friction that coats the surface of the slit. A second layer in contact with the layer of the device may include a polymeric coating with a low coefficient of friction. The layer may include a radioactive isotope.

The surface may be a top surface of the septum that includes a polymeric coating with a low coefficient of friction that coats the surface. A second layer in contact with the layer of the device may include a polymeric coating with a low coefficient of friction. The layer may include a fluorinated silicone. The second layer may be in contact with the layer of the device and may be soluble to a first flush compound and resistant to a second flush compound, while the layer is soluble to a second flush compound and resistant to the first flush compound.

A method of depositing an antimicrobial agent on or in the surface of a medical device may include providing a high temperature resistant tube having a proximal end and a distal end and including multiple holes through its surface, providing a vascular access device housing a septum with a slit that forms two opposing inner surfaces along its length, inserting the distal end of the tube into the slit such that the holes of the distal end face the two opposing inner surfaces of the slit, introducing a coating solution having an antimicrobial agent into the proximal end, and delivering the solution to the two opposing interior surfaces through the holes of the distal end.

The high temperature resistant tube may include metal, a polymer, polytetrafluoroethylene, and/or a material with a low coefficient of friction. The solution may be a solvent that is cured on the two opposing interior surfaces at about 150° C. for about 15 minutes.

A means for accessing the vascular system of a patient may provide means for repressing a pathogen that may reside within the means for accessing the vascular system of a patient. The means for repressing the pathogen may include a slit septum including an antimicrobial agent. The antimicrobial agent may be coated on the surface of the septum and/or compounded, mixed, or integrated with the material of the septum.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
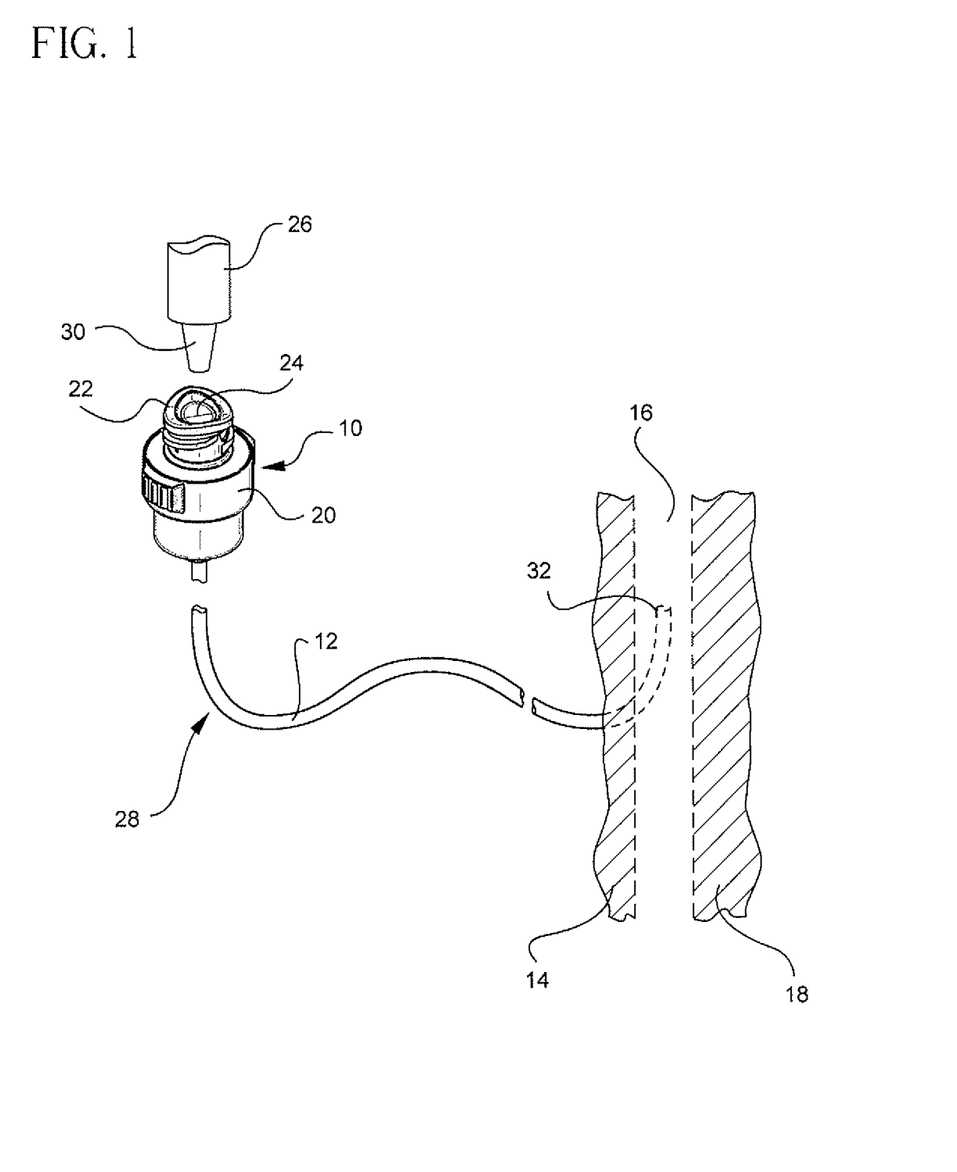
FIG. 1 is a perspective view of an extravascular system connected to the vascular system of a patient.

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 also includes a layer (discussed with reference to the figures below) including at least one antimicrobial agent on or in a surface of the device 10, an extravascular system 28, and/or septum 22. The layer may be compounded or integrated directly into the material of the body of the vascular access device 10, septum 22, and/or system 28. The antimicrobial agent of the layer represses at least one pathogen to decrease the incidence of blood stream infections in patients to whom the vascular access device 10 or any other device on an extravascular system 28 is attached.

As described throughout this specification, pathogens include any agent that causes a disease or otherwise harms or has the potential to harm a patient if received into the vascular system of that patient, including a pathogen, bacterium, parasite, microbe, biofilm, fungus, virus, protein feeding a pathogen, protozoan, and/or other harmful microorganisms and/or agents and products thereof. The layer represses pathogenic activity by any one or combination of the following actions upon a pathogen: removing, dislodging, inhibiting growth, attracting to a location, repelling from a location, degrading, frustrating, killing, preventing growth or proliferation, radiating, and/or any other similar process or action.

A pathogen may enter the device 10 or system 28 in any of a number of ways. For example, a pathogen may reside within the device 10 or system 28 prior to first use. A pathogen may also be introduced into the device 10 from the external surface of the device, the external surface of a separate device 26, and/or the surrounding environment when a structure such as a tip 30 of the separate device 26 is inserted into the device 10 through the slit 24 of the septum 22. A pathogen may be introduced within fluid that is infused into the system from a separate device 26. Finally, a pathogen may be introduced from a blood vessel 16 into the system 28 by entering through the end 32 of the catheter 12 during a blood draw or a period of blood reflux when the device 10 is in use. The layer may thus be placed in or on any surface of the entry, junctions, and/or fluid path of the system 28 in order to repress pathogenic activity, as desired.

Figure 2:
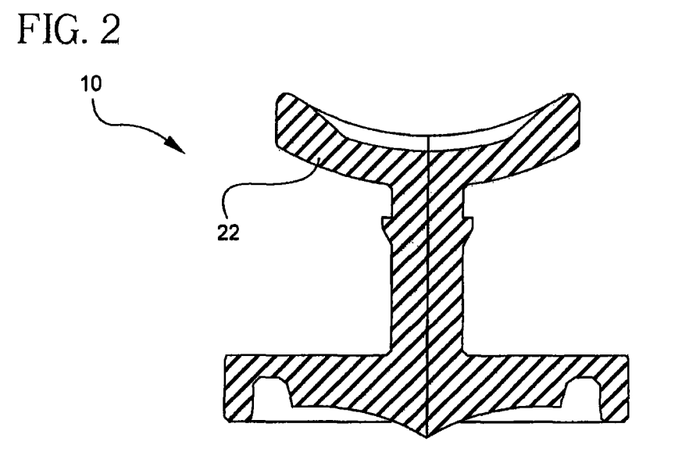
FIG. 2 is a cross section view of a silicone septum containing a radioactive isotope.

Referring now to FIG. 2, a vascular access device 10 includes a septum 22 housed within and against the surface of the body 20 of the vascular access device 10. The septum 22 is an example of a layer on the surface of the body 20 of the vascular access device 10. The septum 22 includes a radioactive isotope mixed within the material of the septum 22. The material of the septum 22 may be formed of a silicone or material with similar properties. The mixture of silicone with a radioactive isotope will provide a material having multiple unstable nuclei that decay, emitting alpha, beta, or gamma rays until stability is reached. During the decay, the material will emit radiation that is harmful to a pathogen. Thus, any pathogen that comes into proximity or contact with the layer described with reference to FIG. 2 will be repressed. The layer of FIG. 2 may include any of the materials or solutions described throughout this specification in order to repress a pathogen.

Various antimicrobial lube oils or other lubricants may be mixed with the silicone of the septum 22, as similarly described with reference to FIG. 2, in order to provide an antimicrobial environment near the septum 22. Such an environment will repress a pathogen as the oils or lubricants naturally seep from the material of the septum 22. For example, a fluorinated silicone may include an antimicrobial agent, for example, triclosan, chlorhexidine, dihydrochloride, and/or chlorhexidine base. The combination of fluorinated silicone with triclosan may form a clear solution with some recrystallization occurring. However, chlorhexidine, dihydrochloride, and chlorhexidine base mixed with fluorinated silicone appear to provide a stable emission of the lubricant from the silicone material during usage of the septum 22.

Each of the three antimicrobial lubes discussed immediately above was placed onto a Whitman No. 2 filter paper punch and sent to determine the zones in which a pathogen is repressed or otherwise inhibited in an area immediately surrounding the two drops of each liquid. These results for various pathogens or bacteria are summarized in Table 1 below. The results indicate that the combination of a silicone with an antimicrobial lubricant is likely to yield an environment capable of repressing a pathogen within a vascular access device 10.

TABLE 1

Zones of Inhibition (measured in millimeters)

| | Pseudomonas aeruginosa | Staphylococcus aureau | Eschericia coli | Candida albicans |
|---|---|---|---|---|
| Control with Fluorinated Silicone | 0 | 0 | 0 | 0 |
| 0.5% Triclosan in Fluorinated Silicone | 2 | 21 | 20 | 2 |
| 0.5% CHB in Fluorinated Silicone | 3 | 5 | 4 | 5 |
| 0.5% CHD in Fluorinated Silicone | 0 | 1 | 0.5 | 0 |

The silicone lube, on the surface of the septum or integrated into the material of the septum, may include any of a number of antifouling materials such as ethylene-oxide, in order to prevent a pathogen such as a bacteria from adhering to the surface of the device 10. Such antifouling materials may be applied to any surface of the device 10. Since pathogens will be unable to adhere to such surfaces, the pathogens will be unable to form a harmful biofilm that could later cause disease to a patient.

Figure 3:
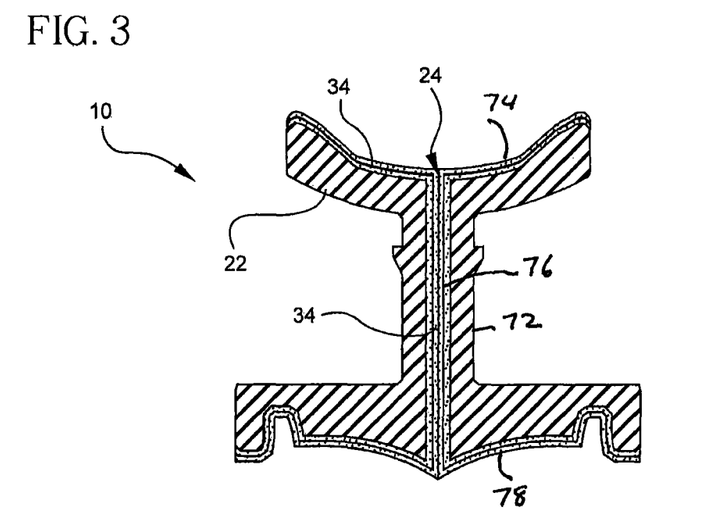
FIG. 3 is a cross section view of a septum containing alternating antimicrobial coatings.

Referring now to FIG. 3, a vascular access device 10 includes at least one layer formed by a septum 22 having alternating coatings 34 of various substances on the surface of the septum 22. Also illustrated in FIG. 3 are surfaces of the septum including outer surface 72, opening surface 74, slit surface 76, and interior surface 78. Each of the alternating coatings 34 is soluble to a different compound to be flushed through the slit 24 of the septum 22 during device 10 use. Further, each of the alternating coatings 34 may include any of the antimicrobial materials and/or solutions described in this specification, including the antimicrobial agents listed in the following Table 2. The agents described in Table 2 may be applied with the various embodiments of the present invention either individually or in any combination with any other agent of Table 2 to provide a pathogenic environment or cocktail. Various agents may be applied to the cocktail in order to entice a pathogen to come into contact with the mixture and subsequently be harmed or killed as a result of the remaining agents in the cocktail.

TABLE 2

| Technology/Company | Antimicrobial Mechanism of Action | Active Ingredient |
|---|---|---|
| Alexidine | Bisbiguanide/Antiseptic | Alexidine |
| AMERICAL (Merodine) | Halogen/Antiseptic | Iodine |
| Angiotech Pharmaceuticals | Antimicrobial/ Antineoplastic | 5-Flurouracil |
| Apacidar (SGA) | Metals & Salts | Silver |
| Arglaes (Giltech) | Metals & Salts | Silver |
| Arrow Howes CHG and AgSD | Bisbiguanide/Antiseptic + antibiotic | Chlorhexidine and Silver Sulfadiazine |
| Bactifree | Metal & Salts | Silver |
| Bacterin | Metal | Silver Hydrogel |
| BASF PVP-I Dusted Gloves BD | Halogen/Antiseptic | Iodine |
| Baxter American Edwards | Antiseptic and Anticoagulant | Benzalkonium Chloride complexed Heparin |
| Benzalkonium Chloride | Quaternary Ammonium/Antiseptic | Benzalkonium Chloride |
| Benzethonium Chloride | Quaternary Ammonium/Antiseptic | Benzethonium Chloride |
| Bioshield (CATO Research) | Halogen/Antiseptic | Iodine |
| BisBAL | Metal, mercury | Bismuth and 2,3 dimercaptopropanol a.k.a. dimercaprol, or British anti-lewisite |
| CATO Research (Bioshield) | Halogen/Antiseptic | Iodine |
| Chlorhexidine (and its salts) | Bisbiguanide/Antiseptic | Chlorhexidine |
| Ciprofloxacin TDMAC Complex BD | Antibiotic | Ciprofloxacin |
| Cooke | TDMAC bound Antibiotic | Any antibiotic |
| Cosmocil | Bisbiguanide/Antiseptic | Cosmocil |
| Cyclodextrin | Nonstick surface | Cyclodextrin |
| Daltex | Bisbiguanide/Antiseptic | Chlorhexidine and Silver Sulfadiazine |
| Dicloxacillin TDMAC Complex BD | Antibiotic | Dicloxacillin |
| EDTA, EGTA | Calcium Chelator | EDTA, EGTA |
| Epiguard (Iodine) | Halogen/Antiseptic | Iodine |
| Epitope (Iodine) | Halogen/Antiseptic | Iodine |

TABLE 2-continued

| Technology/Company | Antimicrobial Mechanism of Action | Active Ingredient |
|---|---|---|
| ExOxEmis | Oxidative enzymes | Myeloperoxidase and Eosinophil Peroxidase |
| Fusidic Acid TDMAC Complex BD | Antibiotic | Fusidic Acid |
| Gamma A Technologies | Specific Antibodies | Specific Antibodies |
| Giltech | Metal & Salts | Silver |
| Glyzinc | Metals & Salts | Zinc |
| Gold | Metal & Salts | Gold |
| Healthshield | Metal & Salts | |
| Heparin-Benzalkonium Chloride | Antimicrobial/Antithrombogenic | |
| Hexyl Bromide | Metals & Salts | Hexyl Bromide |
| Implemed (Ag/Pt) | Metal & Salts | Silver/Platinum |
| Intelligent Biocides | Metals & Salts | Silver |
| Iodine | Halogen/Antiseptic | Iodine |
| Iodine Tincture | Halogen/Antiseptic | Iodine |
| Irgasan | Phenolic/Antiseptic | Triclosan |
| Johnson-Matthey | Metal | Silver |
| Kinetic Concepts | Metals & Salts | Silver |
| Luther Medical | Antibiotic | Polymyxin B |
| Lysozyme | Enzymatic Antibiotic | |
| Mediflex Chlorhexidine Gluconate Tincture | Bisbiguanide/Antiseptic | Chlorhexidine/Isopropanol |
| Merodine | Halogen/Antiseptic | Iodine |
| Microban | Antiseptic Polymer | Triclosan |
| Microbia | Antibiotic | "Natural" polypeptides |
| MicroFre | Metal & Salts | |
| Minocycline Rifampin | Antibiotic | Minocycline Rifampin |
| Minocycline-EDTA | Antibiotic | Minocycline EDTA |
| Morton Bloom | Cidal Lipids | Free fatty acids |
| Novacal | Neutrophil Cidal Factors | Oxidative Enzymes |
| Octenidine | Bisbiguanide/Antiseptic | Octenidine |
| Oligon (Implemed Ag/Pt) | Metal & Salts | Silver/Platinum |
| Olin Chemicals | Metal & Salts | Zinc |
| Omacide | Metal & Salts | Zinc |
| Omni Medical | Heterologous Antibodies | Antibodies |
| Orthophenyl phenol (Lysol) | Phenolic/Antiseptic | Orthophenyl phenol |
| Phosphorus | Antimicrobial Polymer | Phosphorus |
| Polymyxin B (Luther) | Antibiotic | |
| PVP-I (Iodine) | Halogen/Antiseptic | Iodine |
| Quorem Sciences | Cell-signalling | Peptides |
| Rifampin | Antibiotic | Rifampin |
| Sangi Group America | Metal & Salts | Silver |
| SCA | Metal & Salts | Silver |
| Silver Chloride | Metal & Salts | Silver |
| Silver Nitrate | Metal & Salts | Silver |
| Silver Oxide | Metal & Salts | Silver |
| Silver Palladium | Metal & Salts | Silver |
| Spi-Argent | Metal & Salts | Silver |
| Spire | Metal & Salts | Silver |
| Surfacine | Metal & Salts | Silver |
| TCC (Triclocarban) | Phenolic/Antiseptic | Triclocarban |
| TCS (Triclosan) | Phenolic/Antiseptic | Triclosan |
| TDMAC | Antibiotics | Cephazolin, Cipro., Clindamycin, Dicloxacillin, Fusidic Acid, Oxacillin, Rifampin |
| Triclocarban | Phenolic/Antiseptic | Triclocarban |
| Triclosan | Phenolic/Antiseptic | Triclosan |
| Vancomycin | Antibiotic | Vancomycin |
| Vancomycin-Heparin | Antibiotic | Vancomycin-Heparin |
| Vibax | Phenolic/Antiseptic | Triclosan |
| Vitaphore CHG coating | Bisbiguanide/Antiseptic | Chlorhexidine |
| Vitaphore Silver Cuff | Metal & Salts | Silver |
| Zinc | Metal & Salts | Zinc |
| Zinc Omadine | Metal & Salts | Zinc |

Figure 4:
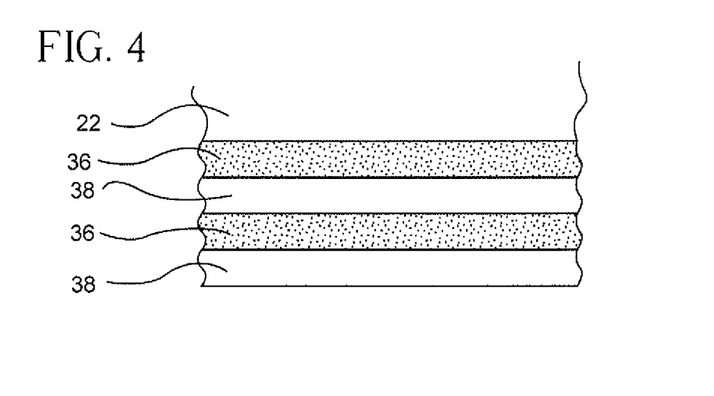
FIG. 4 is a close-up, partial cross section view of the alternating coatings and septum of FIG. 3.

Referring now to FIG. 4, a close-up, partial cross section view of the alternating coatings 34 of FIG. 3 is shown. The alternating coatings 34 include a layer 36 that resides on the surface of the septum 22. The layer 36 includes an antimicrobial agent and is soluble to a flush compound A and resistant to a compound B. A second layer 38 in contact with the layer 36 is resistant to the compound A and soluble to the flush compound B. An additional layer 36 resides on the second layer 38 and an additional second layer 38 resides on the additional layer 36.

Any compound may be used to flush or otherwise dissolve the layers and additional layers 36 and 38 from the surface of the septum 22. For example, saline (e.g., compound A) is often infused through the slit 24 of a septum 22 in order to clean the device 10. After the device 10 is cleaned, a drug (e.g., compound B) may then be infused through the slit 24 of the septum 22 in order to treat a patient.

Figure 5:
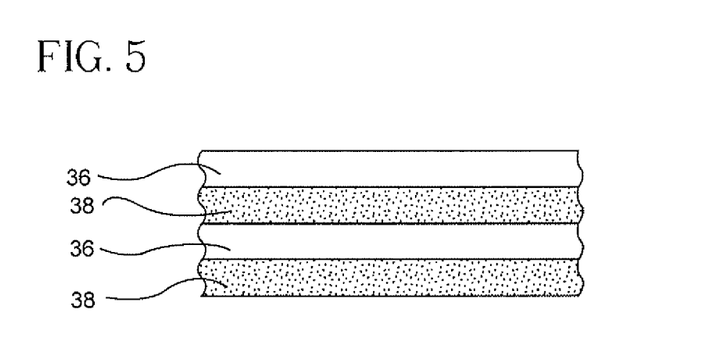
FIG. 5 is a close-up, partial cross section view of the alternating coatings of FIG. 4.

Referring now to FIG. 5, the alternating coatings 34 of FIG. 4 are shown and will be described with reference to an example of a method for dissolving the alternating coatings 34. In use, the various layers of the alternating coatings 34 will be removed as a result of flushing various compounds through the slit 24 of the septum 22. For example, an operator may infuse or flush a medication B through the additional second layer 38, causing the additional second layer 38 to dissolve as the medication comes into contact with the additional second layer 38. However, since the adjacent additional layer 36, is resistant to the flush compound B, i.e., the medication, the additional layer 36 will not dissolve. Layer 36, however, will preferably include an antimicrobial agent that is released when the device 10 is cleaned as saline is flushed into the device, causing layer 36 to dissolve. Since layer 36 is soluble to saline, layer 36 will dissolve. However, since the second layer 38, is not soluble to saline, layer 38 will resist the saline and remain until an operator has completed flushing the device 10 with saline. Since layer 36 includes an antimicrobial agent, the antimicrobial agent will mix with the saline during the flush of the device, and will repress any pathogen that comes into contact with the antimicrobial agent within the device 10 during the flush.

An operator may then reuse the device 10 by infusing a medication to which the next layer is soluble. The operator may then subsequently infuse saline to which the layer 36, directly adjacent to the septum 22 is soluble. The method, or any variations thereof, described with reference to FIG. 5 above may be used with as many alternating coatings of two or more layers of varying solubility and/or resistance to a variety of flush compounds as desired by an operator.

The alternating coatings 34 of the present invention, as described above, may be applied to a variety of embodiments. The following embodiments illustrate various alternatives to the embodiments described with reference to FIGS. 3 through 5 above.

Figure 6:
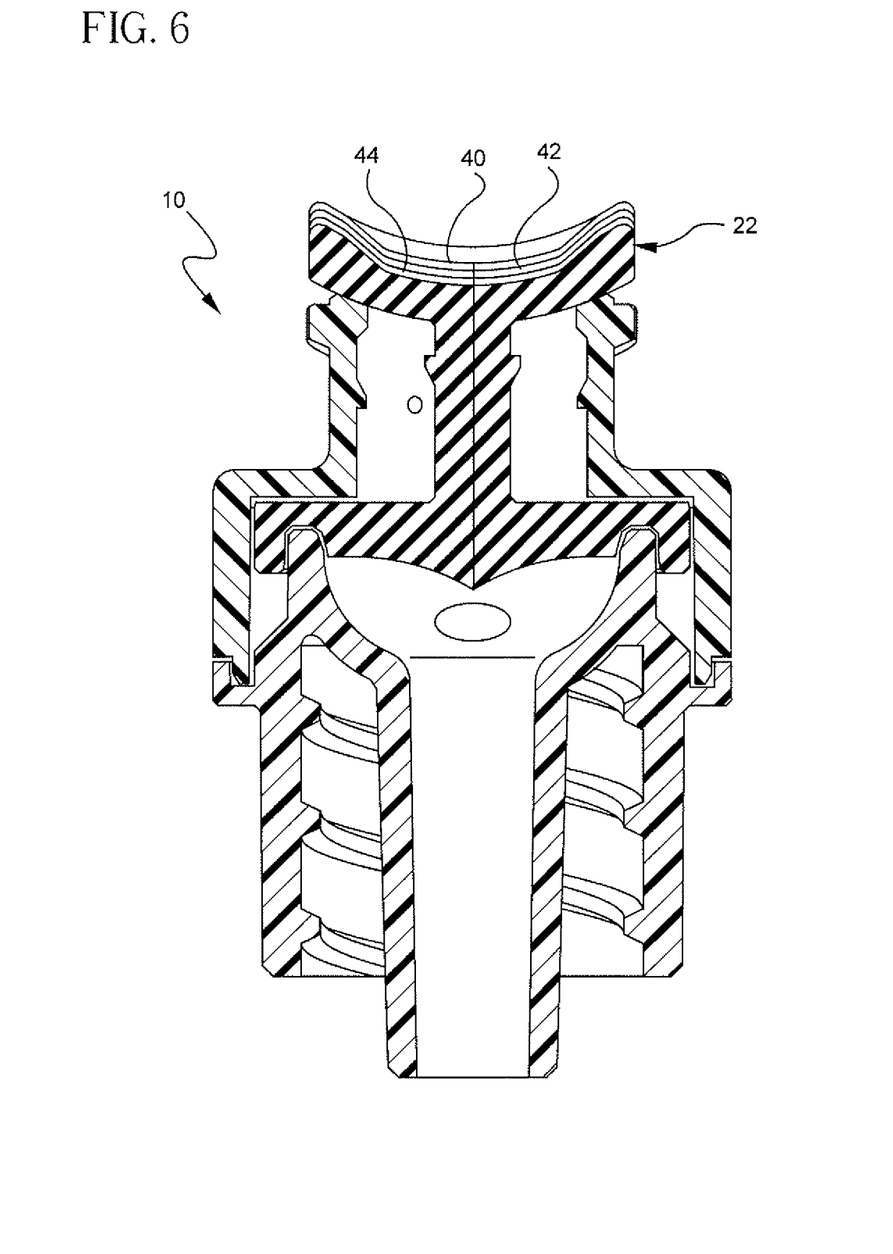
FIG. 6 is a cross section view of a vascular access device having multiple antimicrobial coatings on the top surface of a septum.

Referring now to FIG. 6, a vascular access device 10 includes various antimicrobial coatings on the top surface of the septum 22 of the vascular access device 10. The antimicrobial coatings include a top layer 40, a middle layer 42, and a bottom layer 44. Any number of layers may be placed on the top surface of the septum 22. The septum 22 is formed of an elastomeric material such as silicone.

The antimicrobial coatings may be formed of a variety of materials and solutions and may include any of the antimicrobial agents discussed throughout this specification. For example, a layer of the antimicrobial coating is a polymeric coating with a low coefficient of friction, preferably a low coefficient silicone coating that is either a solvent or a non-solvent. The coating may also be formed of a blend of a low coefficient silicone coating with an antimicrobial agent of greater than or equal to five percent by weight. The coating should be greater than or equal to 0.2 microns thick, will preferably be greater than or equal to 0.5 microns thick, and will most preferably be between 0.5 to 5.0 microns thick.

A number of various coating configurations, one of which is shown in FIG. 6, may be used. For example, the antimicrobial coating may include a single layer or multiple layers of a blend of low coefficient silicone coating with antimicrobial agents that are greater than or equal to five percent by weight. As another example, the bottom layer 44 may be a polymeric coating with a low coefficient to friction, and the top layer 40 may be a blend of low coefficient silicone with antimicrobial agents. As yet another example, the bottom layer 44 may be a blend of low coefficient silicone coating with antimicrobial agents, and the top layer 40 may be a low coefficient polymeric coating. As yet another example, the top layer 40 and bottom layer 44 are formed of a low coefficient polymeric coating, and the middle layer 42 is formed of a low coefficient silicone coating with antimicrobial agents.

Any coating or antimicrobial layer discussed herein may be applied to the septum 22 using various methods. For example, the coating can be spray coated, brush coated, roll coated, or coated with any conventional coating method. After the coating is applied to the septum 22 or to any other layer, the coating may be cured at about 150° C. for 15 minutes. Any number of additional coatings or antimicrobial layers may then be applied to the cured coating.

Figure 7:
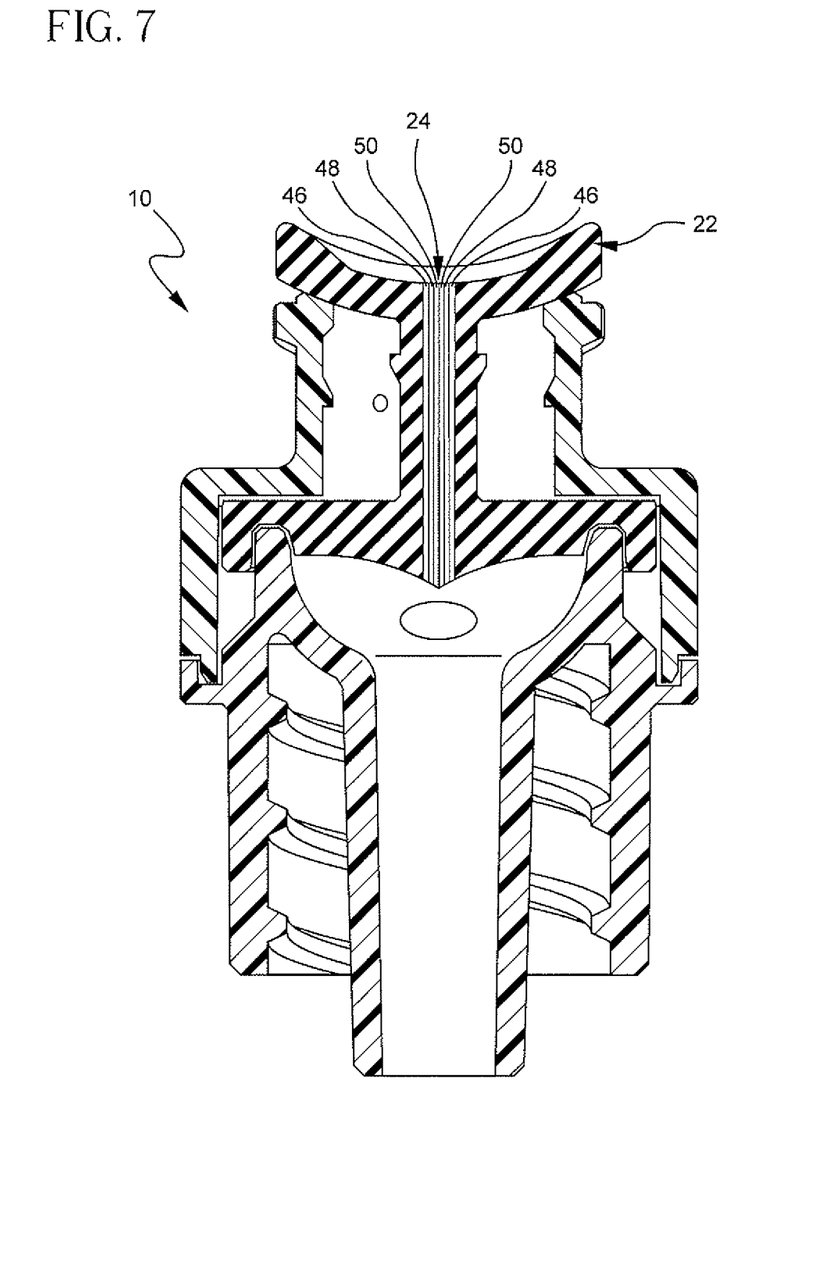
FIG. 7 is a cross section view of a vascular access device having multiple antimicrobial coatings on the interior surface of a septum.

Referring now to FIG. 7, a vascular access device 10 includes multiple antimicrobial coatings or layers located on the surface of the slit 24 of a septum 22. The antimicrobial layers include an inside layer 46, a middle layer 48, and an outside layer 50 situated on the surface of the septum 22. The septum 22 is preferably formed of an elastomer such as silicone.

The coatings 46, 48, and 50, may be formed of a variety of materials and solutions. For example, any of the coatings may be formed of a low coefficient polymeric coating, preferably a low coefficient silicone coating that is a solvent or non-solvent. Any of the coatings may alternatively or additionally be a blend of low coefficient silicone coating with an antimicrobial agent or agents of greater than or equal to five percent by weight. The various antimicrobial layers may include a single or multiple layers of a blend of low coefficient silicone coating with antimicrobial agents. The antimicrobial layers may also include an inside layer 46 that is a low coefficient polymeric coating, and an outside layer 50 that is a blend of low coefficient silicone coating with antimicrobial agents. The antimicrobial layers may also include an inside layer 46 that is a blend of low coefficient silicone with antimicrobial agents, and an outside layer 50 that is a low coefficient polymeric coating. The antimicrobial layers may also include an inside layer 46 and an outside layer 50 that are low coefficient polymeric coatings, and a middle layer 48 that is a blend of low coefficient silicone coating with antimicrobial agents.

The various antimicrobial coatings or layers should be greater than or equal to 0.2 microns thick, are preferably greater than or equal to 0.5 microns thick and are most preferably between 0.5 microns to 5.0 microns thick. Each of the coatings may be cured at about 150° C for 15 minutes. And, each of the coatings may include any number or a combination of a single or multiple antimicrobial agents, including the antimicrobial agents discussed throughout this specification.

Figure 8:
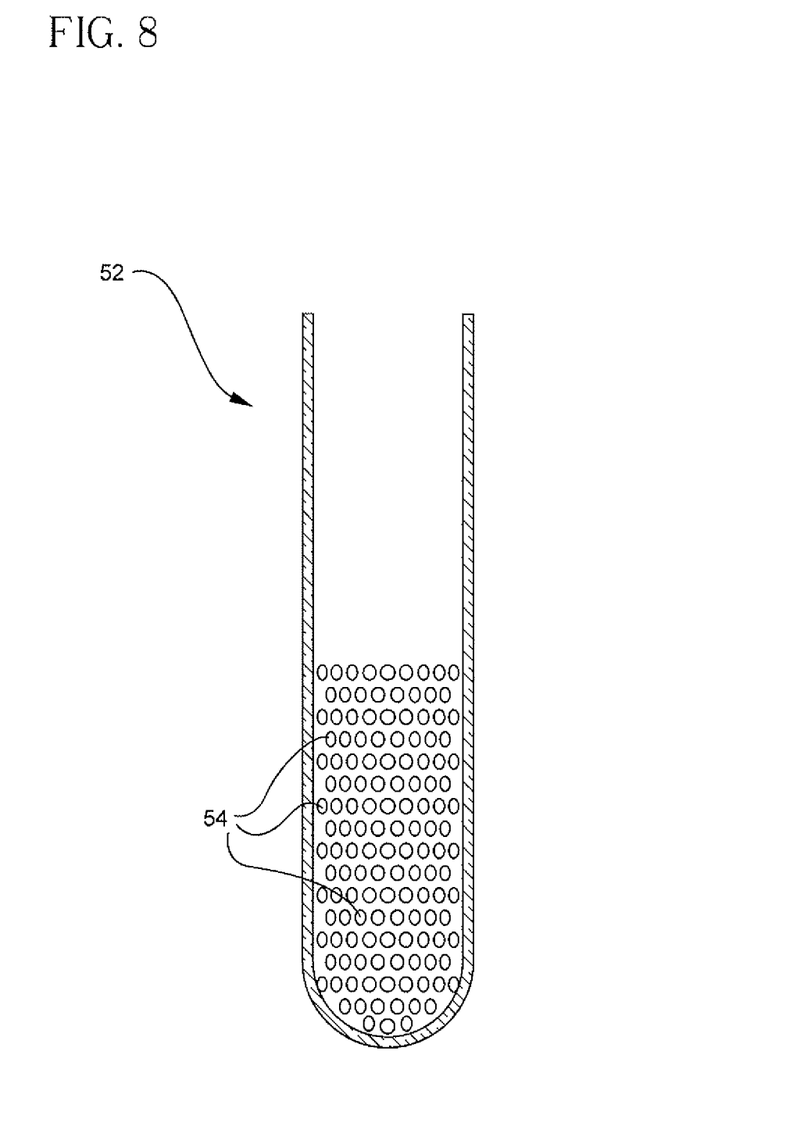
FIG. 8 is a partial side view of a tube having multiple holes at a closed end of the tube.

Referring now to FIG. 8, a tube 52 having multiple holes 54 in an end of the tube 52 may be used to apply the antimicrobial coating to the inner surface of the slit 24 of the device 10 of FIG. 7. The tube 52 is preferably a high temperature resistant tube that has been drilled or otherwise formed to have holes 54 at a closed end of the tube. The location of the holes 54 should correspond with the inner surface of the slit 24 of the septum 22. The tube 52 may then be inserted into the slit 24, and a fluid antimicrobial coating may be infused into the tube 52, transferred through the holes 54, and applied to the surface of the slit 24.

Figure 9:
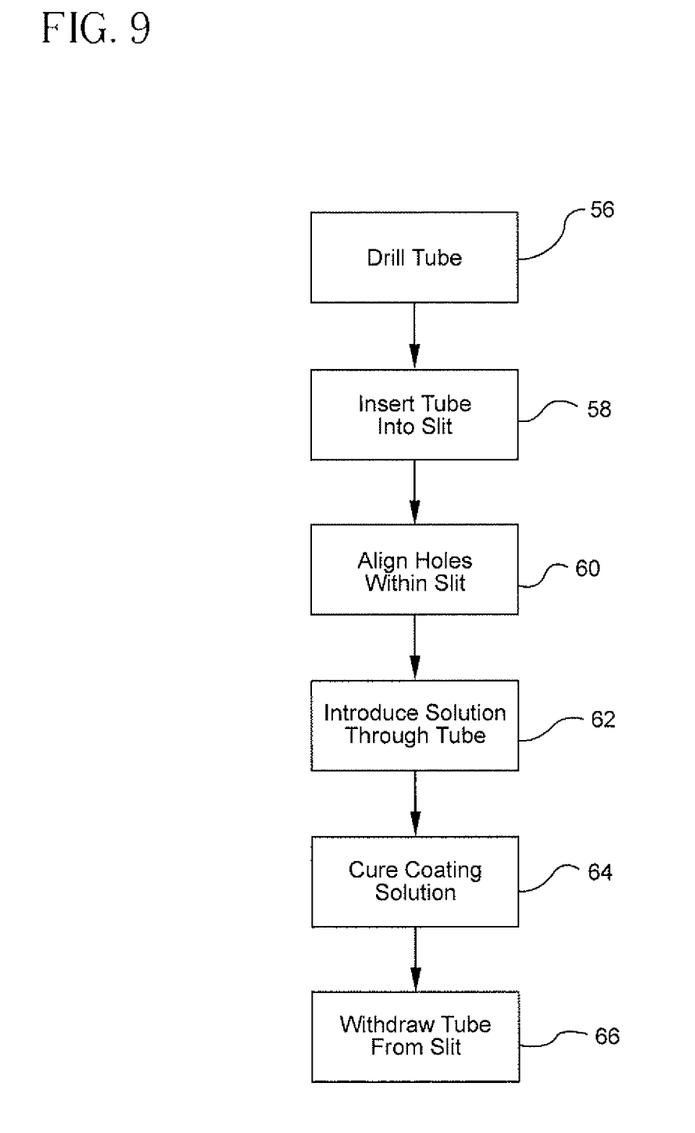
FIG. 9 is a flow diagram illustrating steps for coating the surface of a vascular access device with an antimicrobial coating.

Referring now to FIG. 9, a method of applying at least one antimicrobial coating to the inner surface of a slit 24 is described. A high temperature resistant tube 52 is drilled with holes 54 at the end of the closed tube at step 56. The tube 52 is then inserted into the slit 24 of a septum 22 at step 58. The high temperature resistant tube can be made of a metal, polymer, or similar material, and is preferably manufactured from polytetrafluoroethylene and/or other non-silicone low coefficient material. The tube 52 is then aligned with the slit 24 such that the holes 54 of the tube 52 are in contact with the surface of the slit 24 at step 60. The coating solution (whether solvent or non-solvent) is introduced from the top open end of the tube 52, through the holes 54 of the tube 52, and against the inner surface of the slit 24 at step 62. The coating solution is then cured at 150° C. for 15 minutes at step 64. After curing the coating solution, the tube 52 is withdrawn from the slit 24 at step 66. The above method may be repeated or modified as needed to apply various and multiple antimicrobial coatings to the slit 24 of the device 10.

The embodiments described with reference to FIGS. 2 through 9 may be altered as follows to provide an antimicrobial lube oil coating on the surface of the septum 22. In this embodiment, the coating is a low coefficient lube oil that may be either silicone oil such as polydimethysiloxane or polyphenylsiloxane, or may be a fluorosilicone oil copolymer with a fluoro content from 5 percent to 100 percent. The viscosity of the lube oil should be greater than or equal to 300 cps, and preferably greater than or equal to 900 cps. The lube oil coating is a blend of a lube oil and at least one antimicrobial agent. The lube oil coating should be greater than or equal to 0.10 milligrams per 0.084 square inches, is preferably greater than or equal to 0.40 milligrams per 0.084 square inches, and is most preferably greater than or equal to 0.60 milligrams per 0.084 square inches.

The lube oil coating may be applied to one or more layers of the present invention as discussed above. For example, a lube oil coating may be a single or multiple layers of a blend of lube oil with at least one antimicrobial agent. The layers may also be arranged to include at least one inside layer 46 that is a low coefficient lube oil and at least one outside layer 50 that is a blend of lube oil and at least one antimicrobial agent. Alternatively, the layers may be arranged to include at least one inside layer 46 that is a blend of lube oil and at least one antimicrobial agent, and at least one outside layer 50 that is a low coefficient lube oil. Alternatively, the layers may be arranged to include at least one inner layer 46 and outer layer 50 that is a low coefficient lube oil, and at least one middle layer 48 that is a blend of lube oil and at least one antimicrobial agent.

A method of applying the antimicrobial coatings immediately discussed above may be similar to the method of FIG. 9. However, after the lube oil coating solution is introduced through the tube at step 62, the tube 52 is rotated inside of the slit 24 to ensure the uniform distribution of the coating inside the slit 24. In this manner, the two opposing surfaces of the slit 24 are coated with either an antimicrobial lube oil or other antimicrobial coating solution, consistent with the embodiments described herein.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device comprising:
 a body having an interior lumen;
 a septum housed within the interior lumen of the body, the septum having a slit to allow a separate extravascular device to access the interior lumen, wherein the septum includes an outer surface, an opening surface, a slit surface and an interior surface;
 a first coating material including an antimicrobial agent, disposed on at least one of the opening surface, the slit surface and the interior surface, the first coating material being soluble to a first flush compound and insoluble to a second flush compound, wherein the first coating material includes a solution containing a mixture of the antimicrobial agent and a lube oil, and wherein the first coating material is disposed on the slit surface of the septum; and
 a second coating material disposed on the first coating material, the second coating material being soluble to the second flush compound and insoluble to the first flush compound.

2. The medical device of claim 1, wherein the second coating is a lube oil.

3. The medical device of claim 1, wherein the first and second coating materials are disposed on at least two of the surfaces of the septum selected from the opening surface, the slit surface and the interior surface.

4. The medical device of claim 1, further comprising a plurality of alternating coating material layers disposed on at least one of the opening surface, the slit surface and the interior surface of the septum, wherein the coated septum surfaces comprise alternating layers of the first and second coating materials.

5. The medical device of claim 1, wherein the opening surface of the septum is coated with the first coating material, and wherein the first coating material is coated with the second coating material.

6. The medical device of claim 1, wherein the second coating material includes a fluorinated silicone.

7. The medical device of claim 1, wherein the opening surface, the slit surface and the interior surface form a contiguous contact surface of the septum.

8. A method of repressing pathogens in a vascular access device, comprising:
 providing a vascular access device comprising a body and a septum, the body having an interior lumen and the septum being housed within the interior lumen, the septum having a slit for providing access through the vascular access device, wherein the septum includes an outer surface, an opening surface, a slit surface and an interior surface;
 disposing a first coating material on at least one of the opening surface, the slit surface and the interior surface of the septum, the first coating material being soluble to a first flush compound and insoluble to a second flush compound, the first coating compound having an antimicrobial agent; and
 disposing a second coating material on at least one of the opening surface, the slit surface and the interior surface of the septum, the second coating material being soluble to the second flush compound and insoluble to the first flush compound, wherein the second coating material includes a radioactive isotope.

9. The method of claim 8, further comprising disposing a plurality of alternating coating material layers on at least one of the opening surface, the slit surface and the interior surface of the septum, wherein the coated septum surface comprises alternating layers of the first and second coating materials.

10. The method of claim 8, further comprising disposing the first and second coating materials on at least two of the surfaces of the septum selected from the opening surface, the slit surface and the interior surface.

11. The method of claim 8, further comprising disposing the first and second coating materials to each of the opening surface, the slit surface and the interior surface of the septum.

12. The method of claim 8, wherein the second coating material includes a fluorinated silicone.

13. The method of claim 8, wherein the opening surface, the slit surface and the interior surface form a contiguous contact surface of the septum.

14. A medical device comprising:

a body having an interior lumen;

a septum housed within the interior lumen of the body, the septum having a slit to allow a separate extravascular device to access the interior lumen, wherein the septum includes an outer surface, an opening surface, a slit surface and an interior surface;

a first coating material including an antimicrobial agent, disposed on at least one of the opening surface, the slit surface and the interior surface, the first coating material being soluble to a first flush compound and insoluble to a second flush compound; and a second coating material disposed on the first coating material, the second coating material being soluble to the second flush compound and insoluble to the first flush compound, wherein the second coating material includes a radioactive isotope.

* * * * *